(12) United States Patent
Lukacs

(10) Patent No.: US 7,323,197 B1
(45) Date of Patent: Jan. 29, 2008

(54) CIGARETTE/TEA SYSTEM

(76) Inventor: Maria Lukacs, 4700 Cove Cir., #208, St. Petersburg, FL (US) 33708

( * ) Notice: Subject to any disclaimer, the term of this patent is extended or adjusted under 35 U.S.C. 154(b) by 106 days.

(21) Appl. No.: 11/352,090

(22) Filed: Feb. 10, 2006

(51) Int. Cl.
*A61K 36/00* (2006.01)

(52) U.S. Cl. .................................. 424/725; 424/774

(58) Field of Classification Search ............ None
See application file for complete search history.

(56) References Cited

FOREIGN PATENT DOCUMENTS

RU 2169480 C2 * 6/2001

WO WO 2006/097447 A1 * 9/2006

OTHER PUBLICATIONS

Ginsberg et al. (Nature Medicine (2007), vol. 13, No. 3, pp. 290-294).*
Kamb (Nature Reviews: Drug Discovery (2005), vol. 4, pp. 161-165).*

* cited by examiner

*Primary Examiner*—Susan Coe Hoffman
(74) *Attorney, Agent, or Firm*—Edward P. Dutkiewicz P.A.

(57) ABSTRACT

A cigarette/tea system has a quantity of herbal plant leaves and other herbal plant parts including *pulmonaria officinalia* and *tussilago farfara* and *agrimonia eupatonia* and *petasites hybridus* and *hamamelis virginiana* and *tropaeolum majus*.

6 Claims, 2 Drawing Sheets

FIG 1
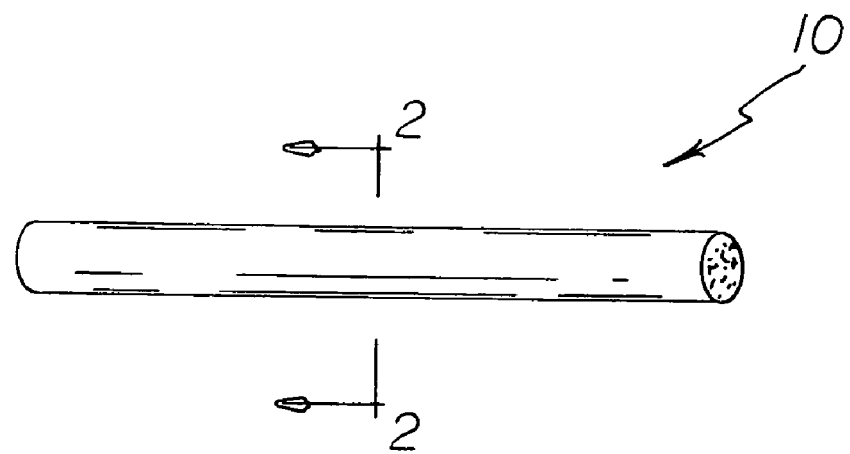
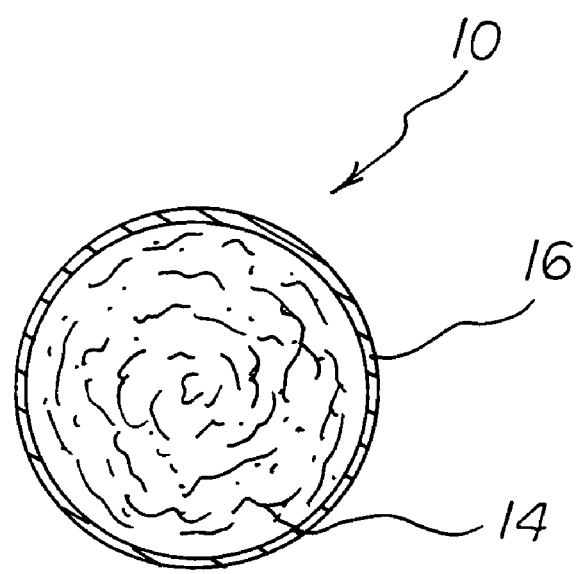
FIG 2

FIG 3
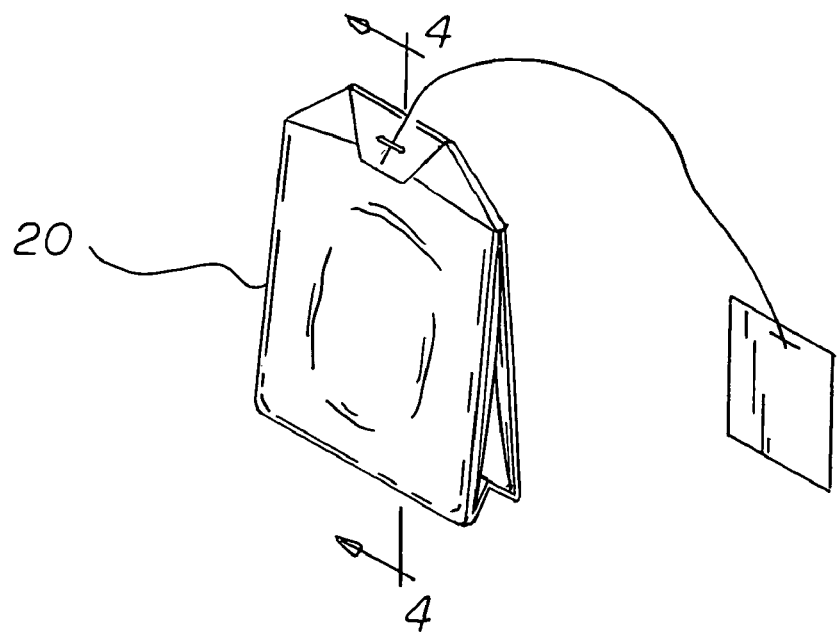
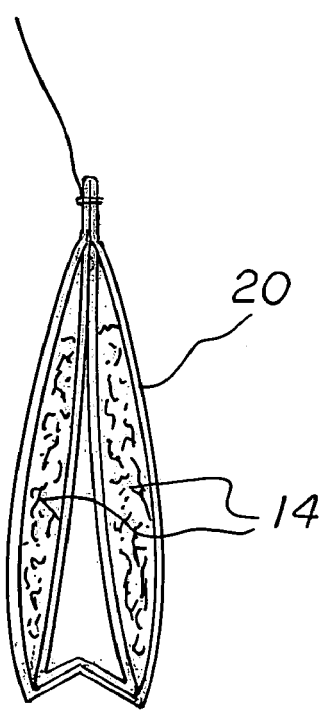
FIG 4

CIGARETTE/TEA SYSTEM

BACKGROUND OF THE INVENTION

1. Field of the Invention

The present invention relates to a cigarette/tea system and more particularly pertains to healing progress and improved health through herbal plant leaves and other herbal plant parts.

2. Description of the Prior Art

The use of cigarette and tea and herbal systems are known in the prior art. More specifically, cigarette and tea and herbal systems previously devised and utilized for the purpose of healing and improving health are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 3,369,552 issued Feb. 20, 1968 to Carroll relates to a Process for Producing a Tobacco Substitute. U.S. Pat. No. 6,475,258 issued Nov. 5, 2002 to Yamashita relates to a Foliar Fertilizer and Method for Using the Same. Lastly, U.S. Pat. No. 6,776,169 issued Aug. 17, 2004 to Zou relates to a *Ginkgo Biloba* L. Leaves Cigarette.

While these devices fulfill their respective, particular objectives and requirements, the aforementioned patents do not describe a cigarette/tea system that allows for healing progress and improved health through herbal plant leaves and other herbal plant parts.

In this respect, the cigarette/tea system according to the present invention substantially departs from the conventional concepts and designs of the prior art, and in doing so provides a system primarily developed for the purpose of healing progress and improved health through herbal plant leaves and other herbal plant parts.

Therefore, it can be appreciated that there exists a continuing need for a new and improved cigarette/tea system which can be used for healing progress and improved health through herbal plant leaves and other herbal plant parts. In this regard, the present invention substantially fulfills this need.

SUMMARY OF THE INVENTION

In view of the foregoing disadvantages inherent in the known types of cigarette and tea and herbal systems now present in the prior art, the present invention provides an improved cigarette/tea system. As such, the general purpose of the present invention, which will be described subsequently in greater detail, is to provide a new and improved cigarette/tea system and method which has all the advantages of the prior art and none of the disadvantages.

To attain this, the present invention essentially comprises a cigarette/tea system for healing progress and improved health through herbal plant leaves and other herbal plant parts for use in cigarettes and teas.

A quantity of herbal plant leaves and other herbal plant parts is first provided. Included are (a) between about 24 percent and 26 percent, preferably about 25 percent, by weight, of *pulmonaria officinalia*, also known as lungwort, and (b) between about 19 percent and 21 percent, preferably about 20 percent, by weight, of *tussilago farfara*, also known as coltsfoot, and (c) between about 19 percent and 21 percent, preferably about 20 percent, by weight, of *agrimonia eupatonia*, also known as agrimony, and (d) between about 19 percent and 21 percent, preferably about 20 percent, by weight, of *petasites hybridus*, also known as butterber, and (e) between about 9 percent and 11 percent, preferably about 10 percent, by weight, of *hamamelis virginiana*, also known as witchhazel, and (f) between about 4 percent and 6 percent, preferably about 5 percent, by weight, of *tropaeolum majus*, also known as nasturtium.

Next provided is a wrapper of one of the herbal plant leaves selected from the quantity of herbal plant leaves. The wrapper is in a hollow cylindrical configuration with a quantity of the herbal plant leaves and other herbal plant parts being chopped up and located within the wrapper for smoking purposes.

Lastly provided is a container. The container is in the form of a paper bag with a quantity of the herbal plant leaves and other herbal plant parts being chopped up and located within the container for brewing purposes.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved cigarette/tea system which has all of the advantages of the prior art cigarette and tea and herbal systems and none of the disadvantages.

It is another object of the present invention to provide a new and improved cigarette/tea system which may be easily and efficiently manufactured and marketed.

It is further object of the present invention to provide a new and improved cigarette/tea system which is of reliable constructions.

An even further object of the present invention is to provide a new and improved cigarette/tea system which is susceptible of a low cost of manufacture with regard to both materials and labor, and which accordingly is then susceptible of low prices of sale to the consuming public, thereby making such cigarette/tea system economically available to the buying public.

Even still another object of the present invention is to provide an cigarette/tea system for healing progress and improved health through herbal plant leaves and other herbal plant parts.

Lastly, it is an object of the present invention to provide a new and improved cigarette/tea system having a quantity of herbal plant leaves and other herbal plant parts including

*pulmonaria officinalia* and *tussilago farfara* and *agrimonia eupatonia* and *petasites hybridus* and *hamamelis virginiana* and *tropaeolum majus*.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of an herbal cigarette constructed in accordance with the principles of the present invention.

FIG. 2 is a cross sectional view taken along line 2-2 of FIG. 1.

FIG. 3 is a perspective illustration of an herbal tea bag constructed in accordance with the principles of the present invention.

FIG. 4 is a cross sectional view taken along line 4-4 of FIG. 3.

The same reference numerals refer to the same parts throughout the various Figures.

DESCRIPTION OF THE PREFERRED EMBODIMENT

With reference now to the drawings, and in particular to FIG. 1 thereof, the preferred embodiment of the new and improved cigarette/tea system embodying the principles and concepts of the present invention and generally designated by the reference numeral 10 will be described.

The present invention, the cigarette/tea system 10 is comprised of a plurality of components. Such components in their broadest context include a quantity of herbal plant leaves and other herbal plant parts including *pulmonaria officinalia* and *tussilago farfara* and *agrimonia eupatonia* and *petasites hybridus* and *hamamelis virginiana* and *tropaeolum majus*. Such components are individually configured and correlated with respect to each other so as to attain the desired objective.

The cigarette/tea system 10, 20 is for healing progress and improved health through herbal plant leaves and other herbal plant parts for use in cigarettes and teas.

A quantity of herbal plant leaves and other herbal plant parts 14 is first provided. Included are (a) between about 24 percent and 26 percent, preferably about 25 percent, by weight, of *pulmonaria officinalia*, also known as lungwort, and (b) between about 19 percent and 21 percent, preferably about 20 percent, by weight, of *tussilago farfara*, also known as coltsfoot, and (c) between about 19 percent and 21 percent, preferably about 20 percent, by weight, of *agrimonia eupatonia*, also known as agrimony, and (d) between about 19 percent and 21 percent, preferably about 20 percent, by weight, of *petasites hybridus*, also known as butterber, and (e) between about 9 percent and 11 percent, preferably about 10 percent, by weight, of *hamamelis virginiana*, also known as witchhazel, and (f) between about 4 percent and 6 percent, preferably about 5 percent, by weight, of *tropaeolum majus*, also known as nasturtium.

Next provided is a wrapper 16 of one of the herbal plant leaves selected from the quantity of herbal plant leaves. The wrapper is in a hollow cylindrical configuration with a quantity of the herbal plant leaves and other herbal plant parts being chopped up and located within the wrapper for smoking purposes.

Lastly provided is a container 20. The container is in the form of a paper bag with a quantity of the herbal plant leaves and other herbal plant parts being chopped up and located within the container for brewing purposes.

It has been found, surprisingly, that the smoking of the cigarettes as described above on a daily basis provides healing progress and improved health. It has been found, surprisingly, that the drinking of the tea as described above on a daily basis also provides healing progress and improved health. Most surprising, however, is the finding that the smoking of such cigarettes and the drinking of such teas simultaneously strengthens the effect and doubles the healing progress.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An herbal leaf system comprising:
a quantity of herbal plant leaves and other herbal plant parts including *pulmonaria officinalis* and *tussilago farfara* and *agrimonia eupatoria* and *petasites hybridus* and *hamamelis virginiana* and *tropaeolum majus*.

2. The system as set forth in claim 1 and further including a wrapper of one of the herbal plant leaves selected from the quantity of herbal plant leaves, the wrapper being in a hollow cylindrical configuration with a quantity of the herbal plant leaves and other herbal plant parts being chopped up and located within the wrapper for smoking purposes.

3. The system as set forth in claim 1 and further including a container with a quantity of the herbal plant leaves and other herbal plant parts being chopped up and located within the container for tea brewing purposes.

4. The system as set forth in claim 1 and further including a wrapper of one of the herbal plant leaves selected from the quantity of herbal plant leaves, the wrapper being in a hollow cylindrical configuration with a quantity of the herbal plant leaves and other herbal plant parts being chopped up and located within the wrapper for smoking purposes, the system further including a container with a quantity of the herbal plant leaves and other herbal plant parts being chopped up and located within the container for tea brewing purposes.

5. The system as set forth in claim 1 wherein the plant leaves and other herbal plant parts includes about 25 percent of *pulmonaria officinalis*, and about 20 percent of *tussilago farfara*, and about 20 percent of *agrimonia eupatoria*, and about 20 percent of *petasites hybridus*, and about 10 percent of *hamamelis virginiana*, and about 5 percent of *tropaeolum majus*.

6. An herbal leaf system comprising, in combination:

a quantity of herbal plant leaves and other herbal plant parts including (a) between about 24 percent and 26 percent, by weight, of *pulmonaria officinalis*, and (b) between about 19 percent and 21 percent, by weight, of *tussilago farfara* and (c) between about 19 percent and 21 percent, by weight, of *agrimonia eupatoria*, and (d) between about 19 percent and 21 percent, by weight, of *petasites hybridus*, and (e) between about 9 percent and 11 percent, by weight, of *hamamelis virginiana*, and (f) between about 4 percent and 6 percent, by weight, of *tropaeolun majus;* a wrapper of one of the herbal plant leaves selected from the quantity of herbal plant leaves, the wrapper being in a hollow cylindrical configuration with a quantity of the herbal plant leaves and other herbal plant parts being chopped up and located within the wrapper for smoking purposes; and a container in the form of a paper bag with a quantity of the herbal plant leaves and other herbal plant parts being chopped up and located within the container for brewing purposes.

* * * * *